(12) United States Patent
Tsukuma et al.

(10) Patent No.: US 7,538,055 B2
(45) Date of Patent: May 26, 2009

(54) TRANSPARENT ZIRCONIA SINTERED BODY

(75) Inventors: Koji Tsukuma, Sagamihara (JP); Isao Yamashita, Odawara (JP)

(73) Assignee: Tosoh Corporation, Shunan-Shi (JP)

( * ) Notice: Subject to any disclaimer, the term of this patent is extended or adjusted under 35 U.S.C. 154(b) by 68 days.

(21) Appl. No.: 11/707,149

(22) Filed: Feb. 16, 2007

(65) Prior Publication Data

US 2007/0197368 A1      Aug. 23, 2007

(30) Foreign Application Priority Data

Feb. 17, 2006  (JP) .............................. 2006-040298
Nov. 10, 2006  (JP) .............................. 2006-305599

(51) Int. Cl.
    *C04B 35/486* (2006.01)
(52) U.S. Cl. .................. 501/103; 501/104; 264/604; 264/673; 433/8
(58) Field of Classification Search ................ 501/103, 501/104; 433/8; 264/604, 673
    See application file for complete search history.

(56) References Cited

U.S. PATENT DOCUMENTS

| 3,432,314 | A | * | 3/1969 | Lynch et al. ................. 501/103 |
| 3,525,597 | A | | 8/1970 | Mazdiyasni et al. |
| 4,758,541 | A | | 7/1988 | Tsukuma |
| 4,902,224 | A | * | 2/1990 | Collins et al. .................. 433/8 |
| 4,915,625 | A | | 4/1990 | Tsukuma et al. |
| 5,011,403 | A | * | 4/1991 | Sadoun et al. ................. 433/8 |
| 5,263,858 | A | | 11/1993 | Yoshida et al. |
| 5,656,564 | A | * | 8/1997 | Nakayama et al. .......... 501/103 |
| 2004/0168610 | A1 | * | 9/2004 | Conrad et al. ................. 106/35 |

FOREIGN PATENT DOCUMENTS

| EP | 0 206 780 A2 | 12/1986 |
| EP | 0 297 908 A1 | 1/1989 |
| JP | 62-91467 A | 4/1987 |
| JP | 1-126267 A | 5/1989 |
| JP | 1-172264 A | 7/1989 |

OTHER PUBLICATIONS

F. W. Vahldiek, "Translucent $ZrO_2$ Prepared at High Pressures", Journal of the Less-Common Metals, vol. 13, Jun. 2, 1967, pp. 530-540.
European Search Report dated Apr. 11, 2007 issued in corresponding European Application No. 07102538.1.

* cited by examiner

*Primary Examiner*—Karl E Group
(74) *Attorney, Agent, or Firm*—Westerman, Hattori, Daniels & Adrian, LLP.

(57) ABSTRACT

A primary sintered body having a density of 95 % or more obtained by sintering a zirconia powder comprising an yttria main component as a stabilizer under ordinary pressure is set in a vessel of a semi-sealed state and subjected to HIP treatment (secondary sintering) at a temperature of from 1,600 to 1,900° C. under a pressure of 50 MPa or higher, and according to need, heated treated in an oxidizing atmosphere, thereby producing a polycrystalline sintered body of zirconia having high transparency of an in-line transmission of 50% or higher.

15 Claims, 3 Drawing Sheets

TRANSPARENT ZIRCONIA SINTERED BODY

FIELD OF THE INVENTION

The present invention relates to a polycrystalline sintered body of zirconia having extremely high transparency.

BACKGROUND OF THE INVENTION

Single crystal of zirconia is transparent, and zirconia single crystal (cubic zirconia) containing about 10 mol % of yttria is conventionally utilized in jewelry goods and the like. On the other hand, it is known that general zirconia sintered body that is polycrystal is opaque. It is known as the cause that pores present between crystal grains and in the grains generate light scattering, and investigations that pores are decreased to impart transparency to polycrystal zirconia sintered body are made until now.

For example, yttria-containing zirconia sintered body having transparency is disclosed in U.S. Pat. No. 3,525,597 (TABLE III) (which is hereinafter referred to as "Patent Document 1"), and it is reported that in-line transmission of a zirconia sintered body containing 6 mol % of $Y_2O_3$ to a visible light is 11% at a thickness of 1.2 mm.

Light-transmitting zirconia containing 2 mol % or more of $Y_2O_3$ and from 3 to 20 mol % of $TiO_2$ is disclosed in JP-A-62-91467 (Claims) (which is hereinafter referred to as "Patent Document 2"), but the presence of $TiO_2$ is essential. (The term "JP-A" as used herein means an "unexamined published Japanese patent application".)

Further, yttria-containing zirconia sintered body having transparency produced under ultrahigh pressure of from 500 to 3,000 MPa is reported in Journal of Less-Common Metals, vol. 13, p 530 (1967) (TABLE II) (which is hereinafter referred to as "Non-Patent Document 1"), and it is reported that in-line transmission of a zirconia sintered body containing 15 mol % of $Y_2O_3$ to a visible light is 10 to 14% at a thickness of 1 mm or less.

Light-transmitting zirconia disclosed in Patent Document 1 and Non-Patent Document 1 each has low in-line transmission, and although there is certain light transmission properties, it has been difficult to say to be transparent.

In general, in-line transmission can be represented by the equation (1), and is determined by scattering coefficient and sample thickness.

$$\ln(T)=\beta t-2\ln(1-R) \quad (1)$$

T: In-line transmission (%)
β: Scattering coefficient ($mm^{-1}$)
t: Sample thickness (mm)
R: Reflectance $R=((1-n)/(1+n))^2$ (n: Refractive index of zirconia)

(Refractive index of yttria-containing zirconia is about 2.2. Details are described in D. L. Wood, APPLIED OPTICS, vol. 29, No. 16, 2485-88 (1990))

For example, when the value (11%) at a sample thickness of 1.2 mm described in Patent Document 1 is converted to 1 mm using the equation (1), the in-line transmission corresponds to 16.6%, and it has been still difficult to say to be transparent.

It is exemplified that the light-transmitting zirconia disclosed in Patent Document 2 has in-line transmission of from 40 to 66% to a visible light of 600 nm at a thickness of 1 mm, and it can be considered to be a transparent sintered body to a certain extend. However, to exhibit such a transparency, it was described that it was essential to contain much $TiO_2$ as 3 to 20 mol %. It is described in the Comparative Example that 8 mol % $Y_2O_3$-containing zirconia sintered body that does not contain $TiO_2$ has in-line transmission of about 7% (thickness 1 mm). It is described that $TiO_2$ promotes grain growth of a sintered body, and there was the problem on, for example, decrease of strength due to that grains become large. Further, as the characteristic that the yttria-containing zirconia possesses, the point that plasma resistance is excellent is exemplified, but there was the problem that the characteristic is impaired by containing $TiO_2$ in large amount.

The present invention provides a stabilized zirconia polycrystalline sintered body that does not contain a transition metal oxide such as $TiO_2$ or contains the same in an extremely reduced amount, uses yttria as a major stabilizer to zirconia, has high transparency and is chemically stable.

SUMMARY OF THE INVENTION

The present inventors have found that a polycrystalline sintered body of a stabilized zirconia that exhibits high transparency is obtained by reducing residual pores contained in a yttria-containing zirconia sintered body by high temperature and high pressure treatment, and further, according to need, heat treating in an oxidizing atmosphere, and have completed the present invention.

That is, the present invention relates to a transparent polycrystalline sintered body comprising zirconia containing from 6 to 15 mol % of yttria as a stabilizer, a transparent polycrystalline sintered body comprising zirconia containing from 6 to 15 mol % of yttria, and preferably at least one of stabilizers other than yttria in the total amount of 2 mol % or less, and its production method.

BRIEF DESCRIPTION OF THE DRAWINGS

FIG. 4A is a cross-sectional view showing the case where the primary sintered body is placed in an alumina vessel with a lid (present invention), FIG. 4B is a cross-sectional view showing the case where the primary sintered body is embedded in a zirconia powder, and placed in an alumina vessel with a lid (present invention), and FIG. 4C is a cross-sectional view showing the case where the primary sintered body is placed in an alumina vessel without a lid (Comparative Example).

DESCRIPTION OF REFERENCE NUMERALS AND SIGNS

Figure 1:
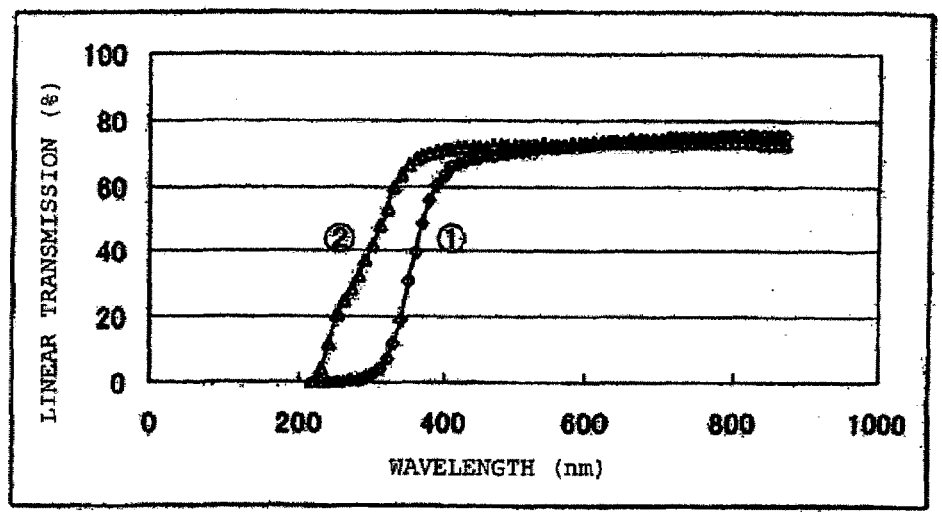
FIG. 1 is a graph showing in-line transmission to a visible light of 1) a polycrystalline sintered body of the present invention (Table 1, Sample No. 2) and 2) a commercially available YSZ single crystal (sample thickness 1 mm).

1: Primary sintered body
2: Alumina vessel
3: Alumina lid
4: Electromelting zirconia powder

DETAILED DESCRIPTION OF THE INVENTION

The stabilizer of zirconia of the present invention mainly comprises yttria, but each oxide of an alkaline earth metal, a lanthanum rare earth metal, scandium, titanium, niobium, tantalum, indium and germanium may be contained as the stabilizer other than yttria in a small amount. When the stabilizer other than yttria is a small amount of 2 mol % or less, it is solid solubilized in a crystal structure similar to yttria, and a stabilized crystal structure similar to yttria-containing zirconia is obtained without adversely affecting other characteristics.

The transparent polycrystalline sintered body of the present invention has high transparency that in-line transmission to a visible light having a wavelength of 550 nm is 50% or more in a sample thickness of 1 mm. Estimating in-line transmission of a complete transparent body having scattering coefficient of zero from the equation (1), it is 75%, and the upper limit of the in-line transmission of the polycrystalline sintered body of the present invention is nearly comparable to the value.

It is preferable that a crystal phase of the transparent polycrystalline sintered body of the present invention comprises a cubic fluorite crystal structure. As a factor that scatters light, there is scattering by grain boundary of a polycrystal, other than residual pores. However, in the case of a cubic crystal having no optical anisotropy, grain boundary scattering is not generated, and it is particularly preferable to exhibit high transparency.

A method of producing the transparent polycrystalline sintered body of the present invention is described below.

The transparent polycrystalline sintered body of the present invention is obtained by molding a zirconia powder containing as a stabilizer, yttria or yttria and 2 mol % or less of other stabilizer, pressureless sintering until a relative density is 95% or more (primary sintering), and then high temperature and high pressure treating by hot isostatic press (HIP) (secondary sintering).

A raw material powder can be molded by applying methods generally used in ceramics, such as press molding, cold isostatic press (CIP) molding, cast molding, extrusion molding and injection molding.

Pressureless sintering (primary sintering) can apply sintering in an atmosphere such as air, oxygen or vacuum. In particular, as the simplest atmosphere, sintering in air is preferable.

It is necessary that the sintering temperature is a temperature until a relative density in a stage before pressure sintering is 95% or more. This is to avoid permeation of an atmosphere gas into the inside of a sintered body when pressureless sintering. The sintering temperature varies depending on characteristics of a raw material powder used, but when a zirconia powder comprising fine particles having a specific surface area of from 5 to 20 m²/g is used, a range of from 1,300 to 1,500° C. can generally be applied.

In the present invention, the transparent polycrystalline sintered body is obtained by further high temperature and high pressure treating (secondary sintering) the sintered body sintered at ordinary pressure, by hot isostatic press (HIP).

When the sintered body obtained by sintering at ordinary pressure (primary sintering) is subjected to HIP treatment, grain diameter of a primary sintered body provided is preferable to be small. The reason is that with decreasing the grain diameter, plastic flow of crystal grains is liable to occur under high pressure, and disappearance of residual pores is accelerated. Crystal grain diameter grows with elevation of sintering temperature in sintering at ordinary pressure. Therefore, as the temperature of sintering at ordinary pressure, it is preferable to be 1,500° C. or lower.

The HIP treatment is conducted for the purpose of disappearing residual pores in the sintered body, and its effect increases with an increase in both temperature and pressure.

When the temperature of the hot isostatic press (HIP) treatment is, for example, 1,500° C., transparency of in-line transmission of about 25% is obtained, but transparency of in-line transmission of 50% or more as in the present invention cannot be achieved. This is due to that disappearance of pores in the sintered body is insufficient.

On the other hand, in the present invention, transparency of in-line transmission of 50% or more is obtained by that temperature of the hot isostatic press (HIP) treatment is 1,600° C. or higher. Grain growth of a sintered body is remarkable with an increase in temperature. A grain diameter is about 4 μm at 1,500° C., a grain diameter is about 10 μm at 1,600° C., grain diameter is about 50 μm at 1,750° C., and a grain diameter is about 100 μm at 1,850° C. Transparency increases with an increase in a grain diameter. However, because excessive grain growth brings about a decrease in strength, the HIP treatment temperature is preferably from 1,600 to 1,900° C., and more preferably from 1,650 to 1,800° C.

Pressure of the HIP treatment is required to be 50 MPa or more. In particular, sufficient effect is obtained at from 100 to 200 MPa.

In the HIP treatment, a pressure medium is not particularly limited, but it is generally preferable to use an argon gas.

In the present invention, when the HIP treatment is conducted with a non-oxidizing gas medium such as an argon gas, a primary sintered body to be set in a HIP apparatus is placed in a ceramic vessel made from, for example, alumina, and treated in a semi-sealed state, not in a completely sealed state, thereby a sintered body having particularly high transparency is obtained. Where treated without forming a semi-sealed state, a sintered body is colored, and becomes opaque or semi-transparent as a whole, or a sintered body is obtained such that a surface layer becomes opaque, and only an interior becomes transparent. On the other hand, in a completely sealed state, a vessel breaks during HIP treatment, and cannot be used any more.

The semi-sealed state intended in the present invention is not a completely sealed atmosphere, but means a state that movement of a medium gas as a pressure medium is suppressed in or out of a ceramic vessel during the HIP treatment. Under the conditions of the present invention, an atmosphere of a medium gas in a HIP treatment apparatus differs from an atmosphere of a medium gas around the primary sintered body in a ceramic vessel.

The semi-sealed state in the present invention does not require a high degree of sealing (airtightness), but is, for example, a sealed state to an extent that is achieved by a state of placing a ceramic flat plate on an opening of an alumina or zirconia crucible or a housing pot.

In the method of the present invention, the primary sintered body in a ceramic vessel may further be embedded in a ceramic powder and be subjected to HIP treatment. The ceramic powder used is not particularly limited so far as it is reducible, and it is not a powder that is sintered in the HIP treatment, and is unable to take out the primary sintered body. For example, a zirconia powder (electromelting zirconia powder) and an alumina powder can be exemplified.

Where HIP treatment is conducted without forming a semi-sealed state, color of a sintered body just after HIP changes in black, whereas where the treatment is conducted in a semi-sealed state of the present invention, blackening of a sintered body does not almost occur, or it can be suppressed to a very pale black-tinted degree.

Where a sintered body is blackened by the conventional method, coloration can be removed to a certain extent by again heating at about 1,000° C. in an oxidizing atmosphere. However, a sintered body having high transparency as in the present invention cannot be formed.

The reason that a sintered body of high transparency is obtained by the method of the present invention is not always clear, but it is considered that when the treatment is conducted without forming a semi-sealed state, a slight amount of carbon component gets mixes in a sintered body, and is gasified by re-heating to form fine pores, thereby transparency is impaired. The carbon component here mainly exemplifies a carbon monoxide gas formed by a reaction between oxygen slightly remained in an argon gas medium and carbon used in a heating element, a heat-insulating material and the like used in HIP apparatus. In the present invention, it is considered that by setting a primary sintered body in a semi-sealed space, contact frequency of the primary sintered body and a carbon monoxide gas and the like is decreased, and contamination with a carbon component in the interior of a sintered body, and reduction of the sintered body and generation of pores due to the contamination can be suppressed.

The sintered body after the HIP treatment obtained by the method of the present invention has small carbon content, and when a part of the sintered body is cut off, and is subjected to a surface carbon analysis with EPMA, the carbon content is not observed, or is observed in a remarkably small amount. Specifically, it is preferable that the carbon content is less than 1 atm %.

Even though the HIP treatment of the present invention is conducted, there is the case that a sintered body just after the treatment is colored slightly. In this case, when the sintered body obtained by the method of the present invention is heat treated at from 1,000 to 1,200° C. in an oxidizing atmosphere, the sintered body having no coloration and having high transparency can be obtained.

The oxidizing atmosphere is an atmosphere containing oxygen, and air atmosphere, an atmosphere having oxygen added thereto, and the like can be applied.

It is preferable that the raw material powder used in the present invention uses an easy-sintering powder that results in a primary sintered body having high density of 95% or higher at from 1,300 to 1,500° C. As physical properties of the powder, it is particularly preferable to have a specific surface area of from 5 to 20 $m^2/g$ and a crystallite diameter of from 10 to 70 nm. As such a powder, for example, the commercially available zirconia powder (a product of Tosoh Corporation, product name: TZ-8Y and the like), and powders prepared by a wet synthesis method such as a hydrolysis method and a neutralization method can be exemplified.

The zirconia polycrystalline sintered body of the present invention shows high transmission to light having a wavelength of from 0.4 to 5 µm over from a visible light to an infrared light, and further has heat resistance that is stable under high temperature of 1,500° C. or higher. Therefore, it is useful to applications such as window materials, lamp tubes for illumination and lamp tubes for infrared heating. Further, because refractive index is high as 2.1 or more, it can be used in high refractive index optical parts, such as lenses and prisms, that cannot be realized by a glass. Further, because $TiO_2$ and the like are not contained in a large amount, resistance to plasma such as a halogen gas is excellent, and it can be used as structural parts of an etcher apparatus that is widely used in the production step of semiconductors and liquid crystal displays. Additionally, it is possible to utilize in applications utilizing sensuousness due to transparent feeling, such as orthodontic brackets and jewelry goods.

The present invention is specifically described below by the Examples, but it should be understood that the invention is not limited to those Examples.

EXAMPLE 1 (SAMPLE NO. 1)

<Raw Material Powder>

8 mol % yttria-containing zirconia powder, a product of Tosoh Corporation (product name: TZ-8Y) was used. The powder had a specific surface area of 15.5 $m^2/g$, a crystallite diameter of 23 nm, and the total amount of impurities other than Y, Zr and 0 of 1 wt % or less.

<Sample Preparation>

Using a die press apparatus and a mold, a pressure of 50 MPa was applied to prepare a molding having a diameter of 20 mm and a thickness of 2 mm. This was placed in a rubber frame, and treated with a cold isostatic press apparatus under a pressure of 200 MPa to form a molding. The molding was sintered in air at each temperature of 1,375° C., 1,400° C. and 1,500° C. for 2 hours to obtain white and opaque primary sintered bodies. Each primary sintered body was placed in an alumina vessel, a lid of a alumina flat plate was placed on an opening of the vessel to form a semi-sealed state, and the vessel was set in a HIP apparatus, followed by treating at a temperature of from 1,600 to 1,750° C. under a pressure of 150 MPa in an argon gas medium. Each sintered body obtained was tinted with an extremely pale black, but maintained transparency. Further, each sintered body was heat treated at 1,100° C. for 2 hours in air to obtain a colorless, transparent polycrystalline sintered body. Those were subjected to surface grinding to have a thickness of 1 mm, and then subjected to a double mirror polishing with diamond abrasive grains.

<Measurement Result>

Densities of the primary sintered body and the HIP treated product, and in-line transmission of the mirror polished sample were measured. The density was obtained from the measurement of weight in water by Archimedes' method. The in-line transmission to a visible light was measured using a 200 model double-beam spectrophotometer, a product of Hitachi, Ltd. Further, the in-line transmission to infrared light was measured using FTIR-8100M, a product of SHIMAZU.

Figure 2:
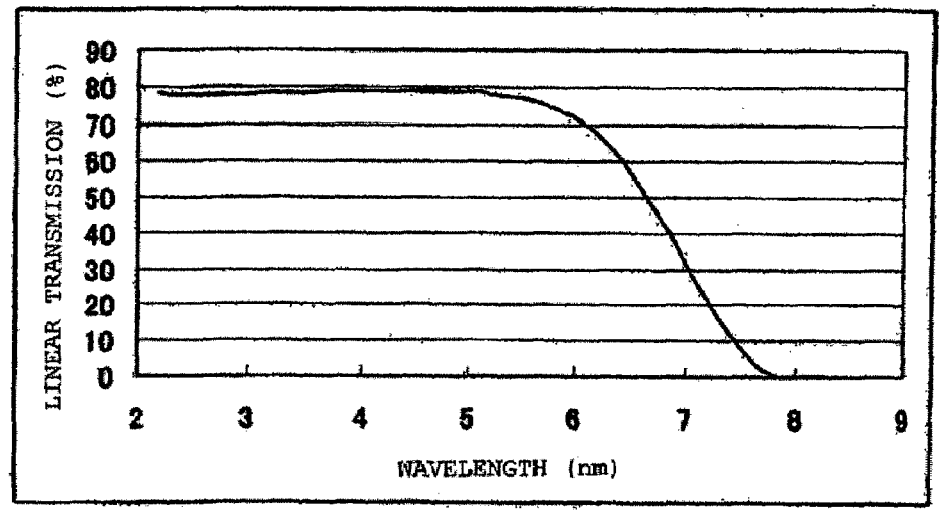
FIG. 2 is a graph showing in-line transmission to a infrared light of a sintered body of the present invention (Table 1, Sample No. 2, thickness 1 mm).

The results are shown in FIGS. 1 and 2. As a reference example, an in-line transmission to a visible light of the commercially available single crystal zirconia (10 mol % $Y_2O_3$-containing $ZrO_2$) was shown (2 in FIG. 1).

As is apparent from FIGS. 1 and 2, the polycrystalline sintered body of the present invention had high transparency nearly equal to a single crystal in a visible light region, and was that a long wavelength infrared light up to about 7 µm permeates.

TABLE 1

| Sample No. | Primary sintering | | HIP treatment | | Polishing treatment |
|---|---|---|---|---|---|
| | Temperature (° C.) | Density (g/cm³) Relative density (%) | Temperature (° C.) | Density (g/cm³) Relative density (%) | In-line transmission at 550 nm (%) |
| 1 | 1375 | 5.68 95.0 | 1750 | 5.98 100 | 72 |
| 2 | 1400 | 5.93 99.1 | 1750 | 5.98 100 | 71 |

TABLE 1-continued

| | Primary sintering | | HIP treatment | | Polishing treatment |
|---|---|---|---|---|---|
| Sample No. | Temperature (° C.) | Density (g/cm³) Relative density (%) | Temperature (° C.) | Density (g/cm³) Relative density (%) | In-line transmission at 550 nm (%) |
| 3 | 1500 | 5.95 99.5 | 1750 | 5.98 100 | 67 |
| 4 | 1400 | 5.93 99.1 | 1600 | 5.98 100 | 52 |

EXAMPLE 2 (SAMPLE NO. 2)

Figure 3:
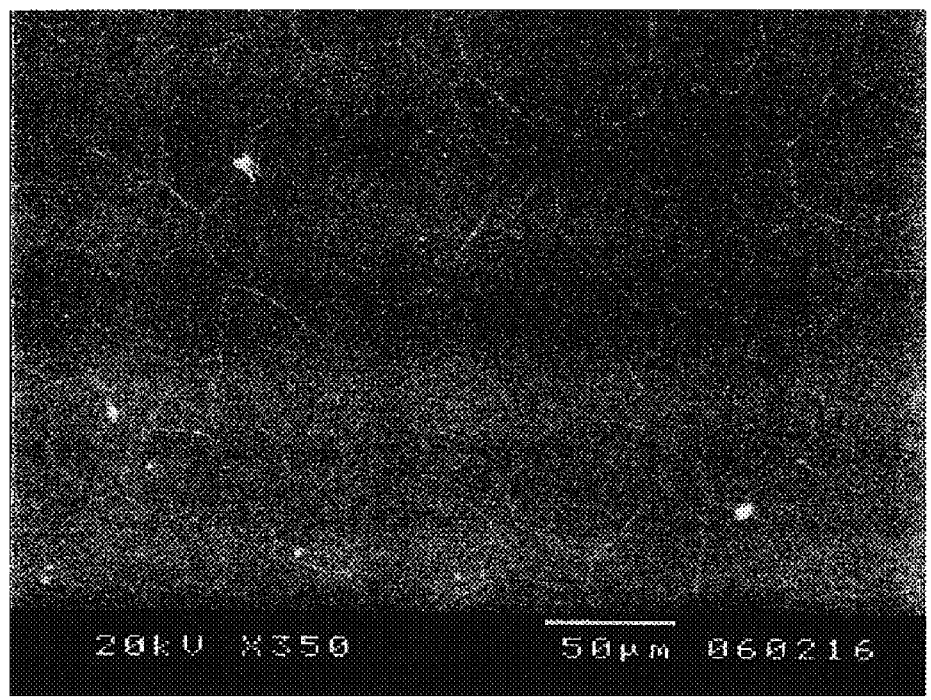
FIG. 3 is an SEM image of a tissue of a polycrystalline sintered body of the present invention (Table 1, Sample No. 2).

Sample No. 2 used for the transmission measurement in Example 1 was heat etched by annealing at 1,400° C. for 1 hour in air, and a tissue of a polycrystalline sintered body was observed. SEM image is shown in FIG. 3. A crystal grain diameter is about 50 μm, and residual pores were not almost present.

EXAMPLE 3 (SAMPLE NO. 3)

<Preparation of Raw Material Powder>

12 mol % yttria-containing zirconia powder was synthesized by hydrolysis method. A predetermined amount of high purity yttria ($Y_2O_3$) powder was added to an zirconium oxychloride aqueous solution (concentration: $ZrO_2$ 0.3 mol/liter), followed by maintaining in a boiling state for 5 days, and hydrated zirconia was precipitated by hydrolysis. After cooling, aqueous ammonia was added to make pH 9, and the precipitate was separated and recovered by filtration. This was calcined at 900° C. for 1 hour. The calcined product was wet ground with a ball mill for 24 hours and dried, and this was used as a raw material powder.

The powder had a specific surface area of 13.8 m²/g, and a crystallite diameter of 25 nm.

<Sample Preparation>

A sample was prepared in the same manner as in Example 1.

<Measurement Result>

The results of measuring densities of a primary sintered body and HIP treated product, and an in-line transmission of a mirror polished sample in the same manner as in Example 1 are shown in Table 2. The 12 mol % yttria-containing zirconia had an in-line transmission nearly equal to the case of 8 mol %.

TABLE 2

| | Primary sintering | | HIP treatment | | Polishing treatment |
|---|---|---|---|---|---|
| Sample No. | Temperature (° C.) | Density (g/cm³) Relative density (%) | Temperature (° C.) | Density (g/cm³) Relative density (%) | In-line transmission at 550 nm (%) |
| 5 | 1400 | 5.88 99.0 | 1750 | 5.94 100 | 71 |
| 6 | 1400 | 5.85 98.5 | 1600 | 5.94 100 | 55 |

EXAMPLE 4 (SAMPLE NO. 4)

A powder containing 1 mol % of each of other rare earth metal oxide $Er_2O_3$ or $Nd_2O_3$ in addition to 7 mol % of yttria was synthesized by hydrolysis method. A raw material powder was prepared in the same manner as in Example 3, except for adding $Er_2O_3$ or $Nd_2O_3$ powder together with a yttria powder to a zirconium oxychloride aqueous solution. Using those powders, samples were prepared in the same manner as in Example 1.

$Er_2O_3$ added sample was obtained as a transparent product colored in pink, and $Nd_2O_3$ added sample was obtained as a transparent product colored in purple. As a result of measurement of an in-line transmission at 550 nm of a mirror polished sample having a thickness of 1 mm, the $Er_2O_3$ added sample showed 70%, and the $Nd_2O_3$ added sample showed 69%.

EXAMPLE 5 (SAMPLE NO. 5)

Regarding all of the samples obtained in Examples 1 and 3, its small amount was crushed in a mortar, and was subjected to X-ray diffraction measurement. From the diffraction pattern, the samples all had a cubic fluorite crystal structure.

EXAMPLE 6 AND COMPARATIVE EXAMPLE 1

Using the same raw (material powder as in Example 1 and using a die press apparatus and a mold, a pressure of 50 MPa was applied to prepare a molding having a diameter of 20 mm and a thickness of 5 mm. This was placed in a rubber frame, and treated with a cold isostatic press apparatus under a pressure of 200 MPa to form a molding. The molding was sintered in air at a temperature of 1,350° C. for 2 hours to obtain a white and opaque primary sintered body.

Figure 4A:
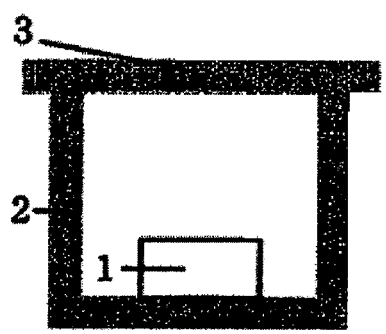
FIGS. 4A to 4C each is a cross-sectional view showing a setting method of a primary sintered body in a HIP apparatus.
Figure 4B:
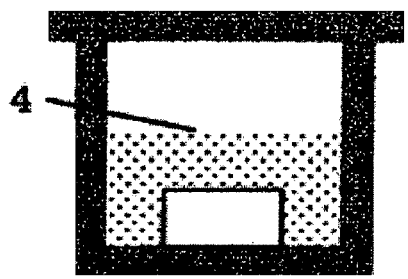
Figure 4C:
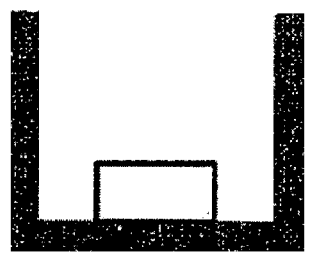

The primary sintered body was set in a HIP apparatus in different three setting states as shown in FIGS. 4A to 4C, and maintained in an argon gas medium at a temperature of 1,350° C. under a pressure of 120 MPa for 1 hour. Temperature was further elevated to 1,650° C., and the primary sintered body was maintained under a pressure of 150 MPa for 1 hour. A method in FIG. 4A is that the primary sintered body is placed in an alumina vessel, and the vessel is closed with a lid of an alumina flat plate, a method in FIG. 4B is that the primary sintered body is further covered with an electromelting zirconia powder, and a method in FIG. 4C is that the primary sintered body is placed in an alumina vessel, but the vessel is not closed with a lid.

Color of the HIP treatment sintered bodies obtained in the methods in FIGS. 4A and 4B did not almost change as compared with color before HIP, and those were transparent. On the other hand, color of the sintered body obtained in the method in FIG. 4C was black. A part of each sintered body was cut off, and subjected to surface carbon analysis by EPMA. Further, the remaining sintered bodies were heat treated in air at 1,000° C. for 2 hours. The sintered bodies obtained by the methods in FIGS. 4A and 4B maintained transparency, but the sintered body obtained by the method in FIG. 4C returned to the original color, but was opaque. Those were subjected to surface grinding to have a thickness of 1 mm, and then subjected to a double mirror polishing with diamond abrasive grains, followed by measuring transmission.

The result of surface carbon analysis and an in-line transmission at 550 nm are shown in Table 3. Carbon was detected from the sintered body obtained by the method in FIG. 4C that is not in a semi-sealed state, and it did not have transparency.

TABLE 3

|  | Setting state of sample | Carbon detected from HIP treatment sample (atm %) | 550 nm transmission (%) |
|---|---|---|---|
| Example 6 | FIG. 4A | <1 atom % | 73 |
|  | FIG. 4B | <1 atom % | 73 |
| Comparative Example 1 | FIG. 4C | 2 atm % | 0 |

While the invention has been described in detail and with reference to specific embodiments thereof, it will be apparent to one skilled in the art that various changes and modifications can be made therein without departing from the spirit and scope thereof.

What is claimed is:

1. A transparent polycrystalline sintered body comprising zirconia containing from 6 to 15 mol % of yttria as a stabilizer and a stabilizer selected from the group consisting of alkaline earth metal oxide, lanthanum rare earth metal oxide, scandium oxide, titanium oxide, niobium oxide, tantalum oxide, indium oxide and germanium oxide present in a total amount of 2 mol % or less,
   wherein said transparent polycrystalline sintered body has an in-line transmission to visible light having a wavelength of 550 nm of 50% or more in a sample having a thickness of 1 mm, and
   wherein grain diameter of the sintered body is larger than 10 μm.

2. The transparent polycrystalline sintered body as claimed in claim 1, wherein a crystal phase is a cubic fluorite structure.

3. A method of producing a transparent polycrystalline sintered body comprising zirconia containing from 6 to 15 mol % of yttria as a stabilizer and a stabilizer selected from the group consisting of alkaline earth metal oxide, lanthanum rare earth metal oxide, scandium oxide, titanium oxide, niobium oxide, tantalum oxide, indium oxide and germanium oxide present in a total amount of 2 mol % or less,
   wherein said transparent polycrystalline sintered body has an in-line transmission to visible light having a wavelength of 550 nm of 50% or more in a sample having a thickness of 1 mm, and
   wherein grain diameter of the sintered body is larger than 10 μm,
   comprising:
   molding a zirconia powder containing a stabilizer and pressureless sintering until a relative density of 95% or more, and then high temperature and high pressure treating by hot isostatic press (HIP).

4. The production method as claimed in claim 3, wherein the pressureless sintering is conducted at a temperature of from 1,300 to 1,5000° C. in an air atmosphere.

5. The production method as claimed in claim 3, wherein the high temperature and high pressure treatment by hot isostatic press (HIP) is conducted at a temperature of from 1,600 to 1,900° C. under a pressure of 50 MPa or more.

6. The production method as claimed in claim 3, wherein the HIP treatment of the primary sintered body having a relative density of 95% or more is conducted by providing a vessel of a semi-sealed state in a HIP treatment apparatus, and providing the primary sintered body in the vessel.

7. The production method as claimed in claim 3, wherein the HIP treatment of the primary sintered body having a relative density of 95% or more is conducted by providing a vessel of a semi-sealed state formed by placing a ceramic flat plate on an opening of a ceramic vessel having the opening in a HIP treatment apparatus, and providing the primary sintered body in the vessel.

8. The production method as claimed in claim 3, wherein the HIP treatment of the primary sintered body having a relative density of 95% or more is conducted by providing a vessel of a semi-sealed state formed by placing a ceramic flat plate on an opening of a ceramic vessel having the opening in a HIP treatment apparatus and providing the primary sintered body in the vessel, and further embedding the primary sintered body in the vessel in a ceramic powder.

9. The production method as claimed in claim 3, wherein the HIP treatment of the primary sintered body having a relative density of 95% or more is conducted by providing a vessel of a semi-sealed state formed by placing a ceramic flat plate on an opening of a ceramic vessel having the opening in a HIP treatment apparatus and providing the primary sintered body in the vessel, and optionally further embedding the primary sintered body in the vessel in a ceramic powder, and wherein a surface carbon concentration of the sintered body after the HIP treatment is less than 1%.

10. The production method as claimed in claim 3, wherein the HIP treatment of the primary sintered body having a relative density of 95% or more is conducted by providing a vessel of a semi-sealed state formed by placing a ceramic flat plate on an opening of a ceramic vessel having the opening in a HIP treatment apparatus and providing the primary sintered body in the vessel, optionally further embedding the primary sintered body in the vessel in a ceramic powder, and after the high temperature and high pressure treatment, further heat-treating at 1,000 to 1,200° C. in an oxidizing atmosphere.

11. The production method as claimed in claim 3, wherein the zirconia powder containing a stabilizer has a purity of 99% or more, a specific surface area of from 5 to 20 m$^2$/g and a crystallite diameter of from 10 to 70 nm.

12. An orthodontic bracket body comprising the transparent polycrystalline sintered body as claimed in claim 1.

13. An orthodontic bracket body comprising the transparent polycrystalline sintered body as claimed in claim 2.

14. The transparent polycrystalline sintered body as claimed in claim 1, wherein said transparent polycrystalline sintered body does not contain a transition metal oxide.

15. The transparent polycrystalline sintered body as claimed in claim 1, wherein said transparent polycrystalline sintered body does not contain Titanium oxide.

* * * * *